United States Patent [19]

Holton et al.

[11] Patent Number: 5,338,872
[45] Date of Patent: Aug. 16, 1994

[54] PROCESS FOR THE PREPARATION OF 10-DESACETOXYBACCATIN III AND 10-DESACETOXYTAXOL AND DERIVATIVES THEREOF

[75] Inventors: Robert A. Holton; Carmen Somoza, both of Tallahassee, Fla.

[73] Assignee: Florida State University, Tallahassee, Fla.

[21] Appl. No.: 5,229

[22] Filed: Jan. 15, 1993

[51] Int. Cl.$^5$ ............................................. C07C 305/14
[52] U.S. Cl. .................................................. 549/510
[58] Field of Search ........................................ 549/510

[56] References Cited

U.S. PATENT DOCUMENTS

| | | | |
|---|---|---|---|
| 4,876,399 | 10/1989 | Holton et al. | 568/817 |
| 4,942,184 | 7/1990 | Haugwitz et al. | 549/510 |
| 4,960,790 | 10/1990 | Stelle et al. | 549/510 |
| 5,200,534 | 4/1993 | Rao | 549/510 |

OTHER PUBLICATIONS

Molander et al, J. Org. Chem., vol. 51, pp. 1135-1138 (1986).
Kusuda et al, Tetrahedron Letters, vol. 30, pp. 2945-2948 (1989).
Inanaga et al, Chem. Lett., pp. 1025-1026 (1991).
Hanessian et al, Tetrahedron Letters, vol. 33, pp. 573-576 (1992).
Klein "Synthesis of 9-Dihydrotaxol: A Novel Bioactive Taxane" Tetrahedron Lett. vol. 34, No. 13, pp. 2047-2050 (1993).
Miller et al., "Antileukemic Alkaloids from Taxus Wallichiana Zucc", J. Org. Chem. 1981, vol. 46, No. 7, pp. 1469-1474.
Chen et al., "Taxol Structure-Activity Relationships: Synthesis and Biological Evaluation of 2-Deoxytaxol", Tetrahedron Lett., vol. 34, No. 20, pp. 3205-3206 (1993).
"Modified Taxols. 5. Reaction of Taxol with Electrophilic Reagents of a Rearranged Taxol Derivative with Tubulin Assembly Activity," Samaranayake, et al., May 15, 1990.
"A Novel Lanthanide-Induced Rearrangement," by Robert A. Holton et al., 1988 American Chemical Society.
"Progress in the Chemistry of Organic Natural Products," 61 pp. 1-11 and 62-81, by D. G. I. Kingston et al., Fortschritte der Chemie organischer Naturstoffe.
Holton et al., "A Synthesis of Taxusin", JACS 110:6558 (1988).
Farina et al., "The Chemistry of Taxanes: Unexpected Rearrangement of Baccatin III During Chemoselective Debenzoylation with Bu$_3$SnOMe/LiCl", Tetrahedron Letters, vol. 33, No. 28, pp. 3979-3982, 1992.

*Primary Examiner*—James H. Reamer
*Attorney, Agent, or Firm*—Senniger, Powers, Leavitt & Roedel

[57] ABSTRACT

A process for the preparation of a 10-desacetoxy and 10-desoxy tetracyclic taxane in which a tetracyclic taxane having a C10 hydroxy or acetoxy substituent is reacted with samarium diiodide.

10 Claims, No Drawings

PROCESS FOR THE PREPARATION OF 10-DESACETOXYBACCATIN III AND 10-DESACETOXYTAXOL AND DERIVATIVES THEREOF

This invention was made with Government support under NIH Grant #CA 42031 and #CA 55131 awarded by the National Institute of Health. The Government has certain rights in the invention.

BACKGROUND OF THE INVENTION

The present invention relates to a process for preparing 10-desacetoxytaxol, 10-desacetoxybacctin III and derivatives of 10-desacetoxytaxol and 10-desacetoxybaccatin III.

Taxol is a natural product extracted from the bark of yew trees. It has been shown to have excellent antitumor activity in in vivo animal models, and recent studies have elucidated its unique mode of action, which involves abnormal polymerization of tubulin and disruption of mitosis. It is currently undergoing clinical trials against ovarian, breast and other types of cancer in the United States and France and preliminary results have confirmed it as a most promising chemotherapeutic agent. The structure of taxol and the numbering system conventionally used is shown below; this numbering system is also applicable to compounds used in the process of the present invention.

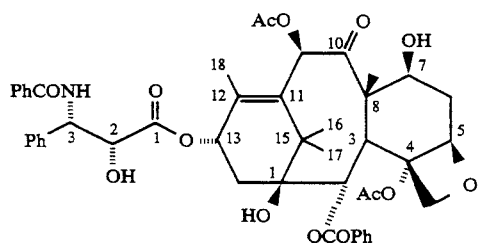

In Colin U. S. Pat. No. 4,814,470, it was reported that a taxol derivative, commonly referred to as taxotere, has an activity significantly greater than taxol. Taxotere has the following structure:

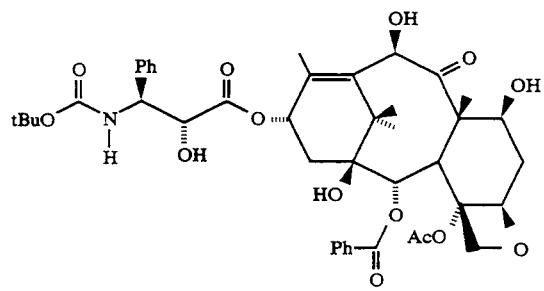

In copending application, U.S. Ser. No. 07/949,449, filed Sep. 22, 1992, it is reported that 10-desacetoxytaxol and related compounds also exhibit anti-tumor activity. Compounds disclosed in this copending application include:

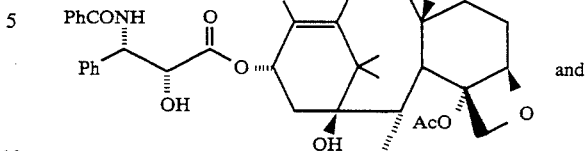

and

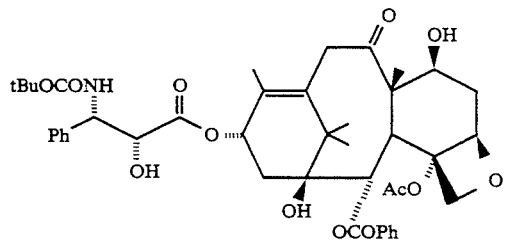

SUMMARY OF THE INVENTION

Among the objects of the present invention, therefore, is the provision of an improved process for preparing 10-desacetoxytaxol, 10-desoxytaxotere, 10-desacetoxybaccatin III and derivatives of 10-descetoxytaxol and 10-desacetoxybaccatin III.

Briefly, therefore, the present invention is directed to a process for the preparation of 10-desacetoxy and 10-desoxy tetracyclic taxanes. According to this process, a tetracyclic taxane having a C10 leaving group such as hydroxy or acetoxy is reacted with samarium diiodide. The C10 leaving group is selectively and nearly quantitatively removed from the tetracyclic taxane.

Other objects and features of this invention will be in part apparent and in part pointed out hereinafter.

DETAILED DESCRIPTION OF THE INVENTION

As used herein "Ar" means aryl; "Ph" means phenyl; "Ac" means acetyl; "R" means alkyl unless otherwise defined; "tBu" means t-butyl; sulfhydryl protecting group" includes, but is not limited to, hemithioacetals such as 1-ethoxyethyl and methoxymethyl, thioesters, or thiocarbonates; "amine protecting group" includes, but is not limited to, carbamates, for example, 2,2,2-trichloroethylcarbamate or tertbutylcarbamate; and "hydroxy protecting group" includes, but is not limited to, ethers such as methyl, t-butyl, benzyl, p-methoxybenzyl, p-nitrobenzyl, allyl, trityl, methoxymethyl, methoxyethoxymethyl, ethoxyethyl, tetrahydropyranyl, tetrahydrothiopyranyl, and trialkylsilyl ethers such as trimethylsilyl ether, triethylsilyl ether, dimethylarylsilyl ether, triisopropylsilyl ether and t-butyldimethylsilyl ether; esters such as benzoyl, acetyl, phenylacetyl, formyl, mono-, di-, and trihaloacetyl such as chloroacetyl, dichloroacetyl, trichloroacetyl, trifluoro- acetyl; and carbonates including but not limited to alkyl carbonates having from one to six carbon atoms such as methyl, ethyl, n-propyl, isopropyl, n-butyl, t-butyl; isobutyl, and n-pentyl; alkyl carbonates having from one to six carbon atoms and substituted with one or more halogen atoms such as 2,2,2-trichloroethoxymethyl and 2,2,2-trichloroethyl; alkenyl carbonates having from two to six carbon atoms such as vinyl and allyl; cycloalkyl carbonates have from three to six carbon atoms such as cyclopropyl, cyclobutyl, cyclopentyl and cyclohexyl; and phenyl or benzyl carbonates optionally substituted on the ring with one or more $C_{1-6}$alkoxy, or nitro. Other hydroxyl, sulfhydryl and amine protecting groups may be found in "Protective Groups in Organic Synthesis" by T. W. Greene, John Wiley and Sons, 1981.

Surprisingly, it has been discovered that tetracyclic taxanes possessing C10 hydroxy or acetoxy substituents may be selectively and nearly quantitatively converted to the corresponding 10-desacetoxy or 10-desoxytaxane. Optionally, the tetracyclic taxane may have a C13 hydroxy or protected hydroxy group or a taxol-like side-chain. Preferably, the tetracyclic taxane has the formula

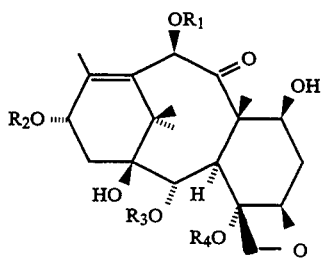

wherein
$R_1$ is hydrogen or acetyl,
$R_2$ is hydrogen, hydroxy protecting group, or

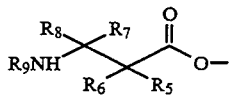

$R_3$ is benzoyl,
$R_4$ is acetyl,
$R_5$ is $-OR_{11}$, $-SR_{12}$, or $-NR_{13}R_{14}$;
$R_6$ is hydrogen, alkyl, alkenyl, alkynyl, aryl or heteroaryl;
$R_7$ and $R_8$ are independently hydrogen, alkl, or alkenyl, alkynyl, aryl, acyl or heteroaryl, provided $R_7$ and $R_8$ are not both acyl;
$R_9$ is $-COR_{15}$, $-COOR_{15}$, $-COSR_{15}$, $-CONR_8_8R_{15}$, or $-SO_2R_{16}$,
$R_{11}$ is hydrogen, alkyl, alkenyl, alkynyl, aryl, heteroaryl, or hydroxy protecting group,
$R_{12}$ is alkyl, alkenyl, alkynyl, aryl, heteroaryl, or sulfhydryl protecting group,
$R_{13}$ is hydrogen, alkyl, alkenyl, alkynyl, aryl, or heteroaryl;
$R_{14}$ is an amino protecting group;
$R_{15}$ is alkyl, alkenyl, alkynyl, aryl, or heteroaryl, and
$R_{16}$ is alkyl, alkenyl, alkynyl, aryl, heteroaryl, $-OR_{15}$, or $-NR_8R_{13}$.

The alkyl groups, either alone or with the various substituents defined hereinabove are preferably lower alkyl containing from one to six carbon atoms in the principal chain and up to 15 carbon atoms. They may be straight or branched chain and include methyl, ethyl, propyl, isopropyl, butyl, isobutyl, tert-butyl, aryl, hexyl, and the like.

The alkenyl groups, either alone or with the various substituents defined hereinabove are preferably lower alkenyl containing from two to six carbon atoms in the principal chain and up to 15 carbon atoms. They may be straight or branched chain and include ethenyl, propenyl, isopropenyl, butenyl, isobutenyl, aryl, hexenyl, and the like.

The alkynyl groups, either alone or with the various substituents defined hereinabove are preferably lower alkynyl containing from two to six carbon atoms in the principal chain and up to 15 carbon atoms. They may be straight or branched chain and include ethynyl, propynyl, butynyl, isobutynyl, aryl, hexynyl, and the like.

The aryl moieties described, either alone or with various substituents, contain from 6 to 15 carbon atoms and include phenyl, α-naphthyl or β-naphthyl, etc. Substituents include alkanoxy, protected hydroxy, halogen, alkyl, aryl, alkenyl, acyl, acyloxy, nitro, amino, amido, etc. Phenyl is the more preferred aryl.

The heteroaryl moieties described, either alone or with various substituents, contain from 5 to 15 atoms and include furyl, thienyl, pyridyl and the like. Substituents include alkanoxy, protected hydroxy, halogen, alkyl, aryl, alkenyl, acyl, acyloxy, nitro, amino, amido, etc. Phenyl is the more preferred aryl.

Most preferably, the tetracyclic taxane is baccatin III, 10-desacetyl baccatin III, taxol, taxotere, or other biologically active tetracyclic taxane having a comparable C13 side chain. Baccatin III and 10-desacetyl baccatin III have the following structures.

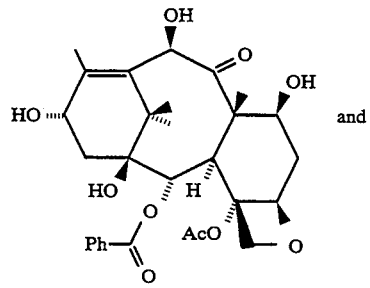

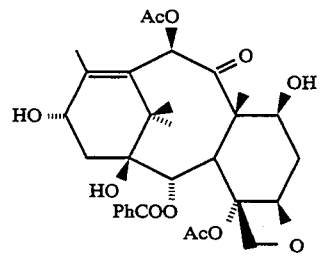

Baccatin III, 10-desacetyl baccatin III and taxol can be separated from mixtures extracted from natural sources such as the needles, stems, bark or heartwood of numerous Taxus species. Taxotere and other biologically active tetracyclic taxanes may be prepared semisynthetically from baccatin III and 10-desacetyl baccatin III as set forth in U.S. Pat. Nos. 4,924,011 and 4,924,012 or by the reaction of a β-lactam and a suitably protected baccatin III or 10-desacetylbaccatin III derivative as set forth in copending U.S. patent application Ser. No. 07/949,107 (which is incorporated herein by reference).

As illustrated in the following examples, the reaction conditions are not narrowly critical. Reaction between the tetracyclic taxane having a C10 leaving group and samarium diiodide may be carried out at 0° C. in a solvent such as tetrahydrofuran. Advantageously, the samarium diiodide selectively abstracts the C10 leaving group; C13 side chains and other substituents on the tetracyclic nucleus remain undisturbed.

The following examples are provided to more fully illustrate the invention.

EXAMPLE 1

10-Desacetoxybaccatin III

To a solution of baccatin III (20 mg; 0.034 mmol) in THF (0.09 mL) at 0° C. under nitrogen was added a solution of SmI$_2$ (0.1M; 0.9 mL; 0.09 mmol) in THF. After stirring 45 minutes at 0° C. the flask was opened to the air, and the reaction mixture diluted with ethyl acetate (10 mL). The mixture was poured into aqueous HCl (0.2N; 25 mL), extracted with ethyl acetate, and the extract was washed successively with saturated aqueous NaHCO$_3$ and brine, dried over Na$_2$SO$_4$ and evaporated. The product was isolated by flash chromatography (SiO$_2$; 80% ethyl acetate-hexanes) affording 16.6 mg (92%) of 10-desacetoxybaccatin III which was recrystallized from CHCl$_3$-hexanes. mp 230°–232° C. $[\alpha]^{25}D = -103.6$ (c=0.00195, CHCl$_3$). IR (cm$^{-1}$): 3100, 2970, 2950, 2900, 1750, 1710, 1460, 1370, 1320, 1270, 1255, 1110, 980, 890, 760, 700. $^1$H-nmr (500 MHz, CDCl$_3$) d 8.11 (dd; 2H; J=8.4, 1.2 Hz; o-Bz); 7.61 (dt; 1H; J=7.5, 1.2 Hz; p-Bz); 7.48 (brt; 2H; J=7.8 Hz; m-Bz); 5.66 (br d; 1H; J=6.9 Hz; H-2b); 4.98 (br dd; 1H; J=9.4,2; H-5a); 4.83 (br; 1H; w½19 Hz; H-13b); 4.34 (dt; 1H; J=11.2, 7.8 Hz; H-7a); 4.31 (br d; 1H;J=8.4 Hz; H-20a); 4.17 (br d; 1H; J=6.9 Hz; H-3a); 4.15 (dd; 1H; J=8.4, 1 Hz; H-20b); 3.84 (d; 1H; J=15.6 Hz; H-10a); 3.46 (ddd; 1H; J=15.6, 3.7, 1.6 Hz; H-10b); 2.64 (ddd; 1H; J=14.4, 9.4, 6.9 Hz; H-6a); 2.29 (s; 3H; 4-OAc); 2.28 (m; 2H; H-14a and H-14b); 1.95 (t; 3H; J=1.6 Hz; 18-Me); 1.94 (d, 1H; J=6.8 Hz; 13-OH); 1.79 (ddd; 1H; J=14.4, 11.2, 2.1 Hz; H-6b); 1.64 (s; 3H; 19-Me); 1.58 (s; 1H; 1-OH); 1.38 (d; 1H; J=7.8 Hz; 7-OH); 1.13 (s, 3H; 16-Me); 1.06 (s, 3H; 17-Me).

EXAMPLE 2

7-Triethylsilyl-10-desacetoxybaccatin III

To a stirred solution of 10-desacetoxybaccatin III (10.0 mg; 0.019 mmol) in anhydrous pyridine (0.05 mL) at room temperature and under nitrogen, triethylchlorosilane (15 L; 0.09 mmol) was added and the resulting mixture was stirred at room temperature for 48 h. After diluting with ethyl acetate (5 mL) the mixture was poured into saturated aqueous NaHCO$_3$ (25 mL) and extracted with ethylene acetate. The extract was washed successively with water, 10% aqueous CuSO$_4$ and brine, dried over Na$_2$SO$_4$ and evaporated. The product was purified by flash chromotagraphy (SiO$_2$; 40% EA-hexanes) affording 11.1 mg (91%) of 7-thiethylsilyl-10-desacetoxybaccatin III.

EXAMPLE 3

10-Desacetoxytaxol

To a stirred solution of taxol (35 mg; 0.041 mmol) in THF (0.1 ml) at 0° C. under nitrogen was added a solution of SmI$_2$ (0.1M; 1.0 mL; 0.10 mmol) in THF. After stirring 45 minutes at 0° C. the flask was opened to the air and the reaction mixture diluted with ethyl acetate (10 mL). The mixture was poured into aqueous HCl (0.2N; 25 mL), extracted with ethyl acetate, and the extract was washed successively with saturated aqueous NaHCO$_3$ and brine, dried over Na$_2$SO$_4$ and evaporated. The product was isolate by flash chromatography (SiO$_2$; 80% ethyl acetate-hexanes) affording 29.4 mg (90%) of 10-desacetoxytaxol.

What I claim is:

1. A process for the preparation of a 10-desacetoxy or 10-desoxy tetracyclic taxane comprising reacting a tetracyclic taxane having a C9 keto substituent and a C10 hydroxy or acetoxy substituent with samarium diiodide.

2. The process of claim 1 wherein the tetracyclic taxane has a C10 hydroxy substituent.

3. The process of claim 1 wherein the tetracyclic taxane has a C10 acetoxy substituent.

4. The process of claim 1 wherein the tetracyclic taxane has the formula

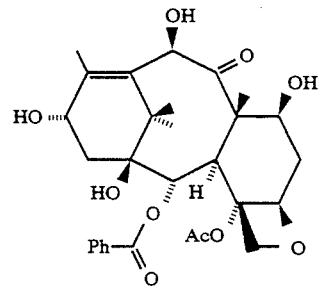

wherein ph is phenyl and Ac is acetyl.

5. The process of claim 1 wherein the tetracyclic taxane has the formula

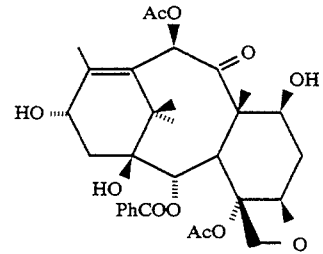

wherein Ph is phenyl and Ac is acetyl.

6. The process of claim 1 wherein the tetracyclic taxane has the formula

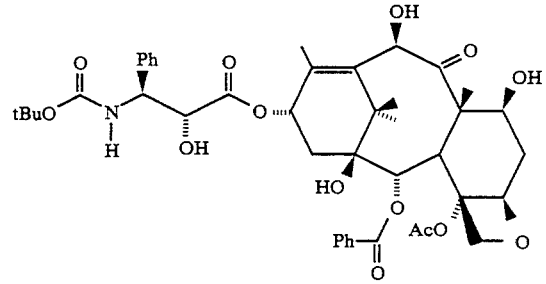

wherein tBu is tert-butyl, Ph is phenyl and Ac is acetyl.

7. The process of claim 1 wherein the tetracyclic taxane has the formula

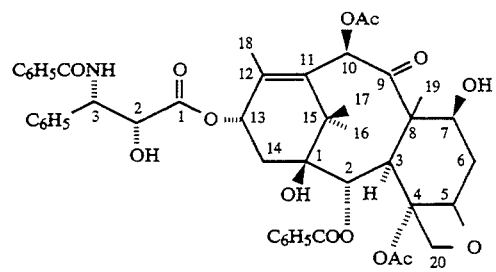

wherein Ac is acetyl.

8. A process as set forth in claim 1 wherein the reaction is carried out at 0° C. in tetrahydrofuran.

9. A process as set forth in claim 4 wherein the reaction is carried out at 0° C. in tetrahydrofuran.

10. A process as set forth in claim 5 wherein the reaction is carried out at 0° C. in tetrahydrofuran.

* * * * *

UNITED STATES PATENT AND TRADEMARK OFFICE
CERTIFICATE OF CORRECTION

PATENT NO. : 5,338,872
DATED : August 16, 1994
INVENTOR(S) : Robert A. Holton and Carmen Somoza It is certified that error appears in the above-identified patent and that said Letters Patent is hereby corrected as shown below:

In column 1, lines 35-43, the formula should read

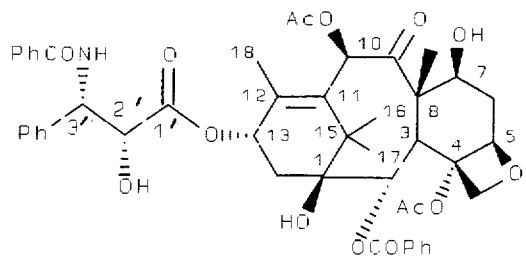

In column 2, lines 1-10, the formula should read

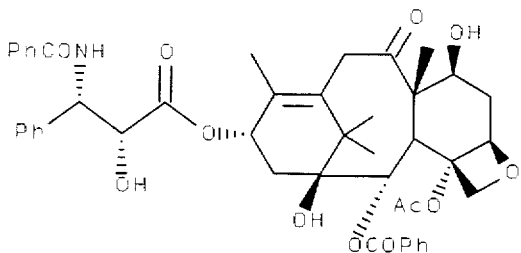

UNITED STATES PATENT AND TRADEMARK OFFICE
CERTIFICATE OF CORRECTION

PATENT NO. : 5,338,872

DATED : August 16, 1994

INVENTOR(S) : Robert A. Holton and Carmen Somoza

It is certified that error appears in the above-identified patent and that said Letters Patent is hereby corrected as shown below:

In column 2, lines 11-20, the formula should read

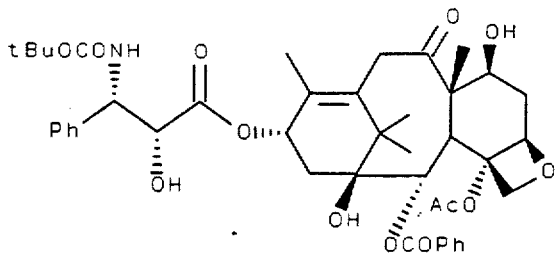

In column 6, claim 7, lines 52-60, the formula should read

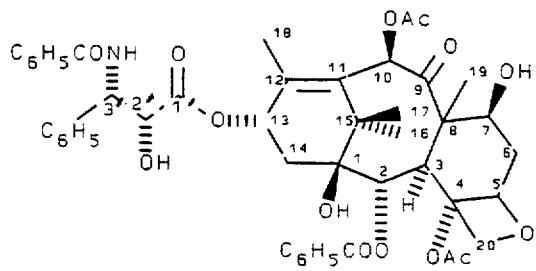

Signed and Sealed this

First Day of July, 1997

Attest:

BRUCE LEHMAN

Attesting Officer

Commissioner of Patents and Trademarks